United States Patent [19]
Foo et al.

[11] Patent Number: 6,020,516
[45] Date of Patent: Feb. 1, 2000

[54] HYDROCYANATION OF DIOLEFINS AND ISOMERIZATION OF NONCONJUGATED 2-ALKYL-3-MONOALKENENITRILES

[75] Inventors: Thomas Foo; James Michael Garner, both of Wilmington, Del.; Wilson Tam, Boothwyn, Pa.

[73] Assignee: E. I. du Pont de Nemours and Company, Wilmington, Del.

[21] Appl. No.: 09/121,146

[22] Filed: Jul. 23, 1998

Related U.S. Application Data

[60] Provisional application No. 60/054,022, Jul. 29, 1997.
[51] Int. Cl.[7] .................................................. C07L 253/00
[52] U.S. Cl. ............................................... 558/338
[58] Field of Search .............................. 558/338

[56] References Cited

U.S. PATENT DOCUMENTS 5,821,378  10/1998  Foo et al. ................................ 558/338

FOREIGN PATENT DOCUMENTS

| | | | |
|---|---|---|---|
| 19717359 | 11/1997 | Germany | C07F 9/145 |
| WO 96/11182 | 4/1996 | WIPO . | |
| WO 96/22968 | 8/1996 | WIPO . | |
| WO 97/33892 | 9/1997 | WIPO . | |

*Primary Examiner*—Johann Richter
*Assistant Examiner*—Joseph Murray

[57] ABSTRACT

Improved liquid phase process useful in the hydrocyanation of diolefinic compounds to produce nonconjugated acyclic nitrites and to the liquid phase process of isomerization of the nitriles to, among other things, 3- and/or 4-monoalkene linear nitrites. The improvement involves conducting the process in the presence of zero-valent nickel and a multidentate phosphite ligand.

26 Claims, No Drawings

HYDROCYANATION OF DIOLEFINS AND ISOMERIZATION OF NONCONJUGATED 2-ALKYL-3-MONOALKENENITRILES

This application claims the priority benefit of U.S. Provisional Application 60/054,022, filed Jul. 29, 1997.

FIELD OF THE INVENTION

This invention generally relates to an improved liquid phase process useful in the hydrocyanation of diolefinic compounds to produce nonconjugated acyclic nitriles and to a liquid phase process of isomerization of said nitriles to, among other things, 3- and/or 4-monoalkene linear nitriles. The improvement resides in conducting the processes in the presence of zero-valent nickel and a multidentate phosphite ligand.

BACKGROUND OF THE INVENTION

Catalytic hydrocyanation systems, particularly pertaining to the hydrocyanation of olefins, are known in the art. For example, liquid phase systems useful for the hydrocyanation of butadiene to form pentenenitriles (PN) are known in the art. For example, Drinkard, U.S. Pat. No. 3,496,215, discloses the hydrocyanation of butadiene using nickel catalysts with monodentate phosphite ligands. As used in this patent, and as will be used herein, the term "pentenenitrile" is intended to mean cyanobutene. Likewise, "butenenitrile" means cyanopropene. Bidentate phosphite ligands complexed to zero-valent nickel and platinum are known to be useful in the liquid phase hydrocyanation of butadiene, as described by Baker et al., *J Chem. Soc., Chem. Commun.*, 1991, 803–804.

The pentenenitriles so formed are subjected to further hydrocyanation and/or isomerization to form adiponitrile (ADN), a commercially important material in the manufacture of nylon. For example, Drinkard, U.S. Pat. No. 3,536,748, discloses the liquid phase isomerization of 2-methyl-3-butenenitrile in the presence of a zero valent nickel complex and Chia, U.S. Pat. No. 3,676,481, discloses an improvement additionally utilizing tri(hydrocarbyl)boron promoters.

The hydrocyanation of activated olefins such as conjugated olefins (e.g., butadiene and styrene) and strained olefins (e.g., norbornene) proceeds without the use of a Lewis acid promoter, while hydrocyanation of unactivated olefins such as 1-octene and 3-pentenenitrile normally require the use of a Lewis acid promoter. Teachings regarding the use of a promoter in the hydrocyanation reaction appear, for example, in U.S. Pat. No. 3,496,217.

Certain multidentate phosphite ligands useful in the present invention for the hydrocyanation of diolefins have been used for the hydrocyanation of monoolefins. Commonly assigned, WO 95/14659 and U.S. Pat. No. 5,512,696, disclose bidentate phosphite ligands preferably used in combination with a Lewis acid promotor to hydrocyanate monoolefins.

The present invention provides for an improved process for the hydrocyanation of diolefinic compounds, such as butadiene, and isomerization of nonconjugated acyclic nitrites without the need for Lewis acid promoters utilizing zero-valent nickel and a multidentate phosphite ligand wherein there is at least one 1-naphthol terminus present. Other objects and advantages of the present invention will become apparent to those skilled in the art upon reference to the detailed description of the invention which hereinafter follows.

SUMMARY OF THE INVENTION

The present invention provides an improved process for the liquid phase hydrocyanation of diolefinic compounds and isomerization of the resulting nonconjugated acyclic nitrites comprising, reacting an acyclic aliphatic diolefinic compound, preferably butadiene, with a source of HCN, wherein the improvement comprises conducting the hydrocyanation and/or isomerzation in the presence of a catalyst precursor composition comprising zero-valent nickel and at least one multidentate phosphite ligand selected from the group consisting of compounds represented by Formulas I, II, III, IV, V, VI, VII, VIII, IX and X, as set forth below:

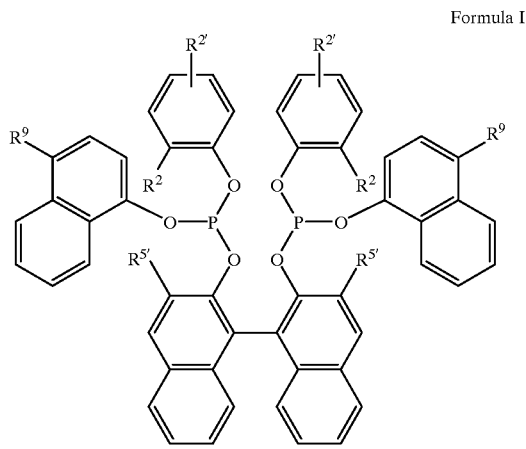

Formula I

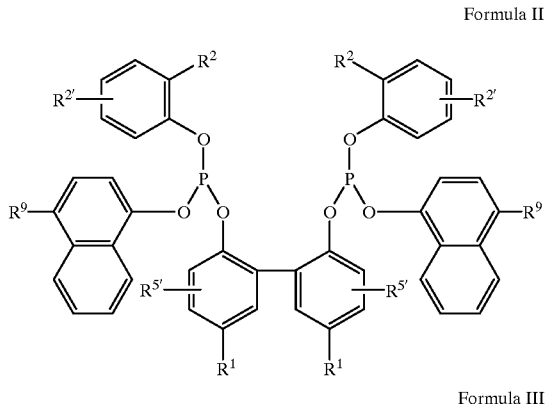

Formula II

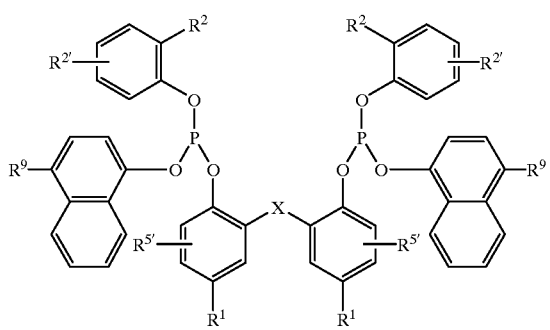

Formula III

Formula IV

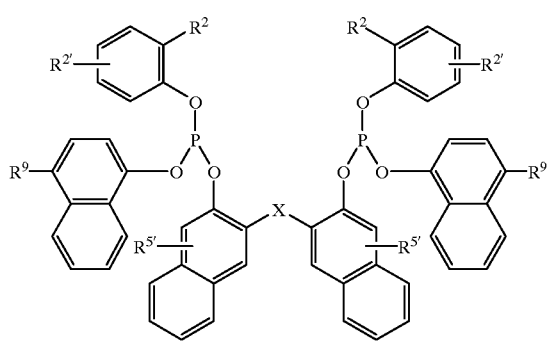

Formula V

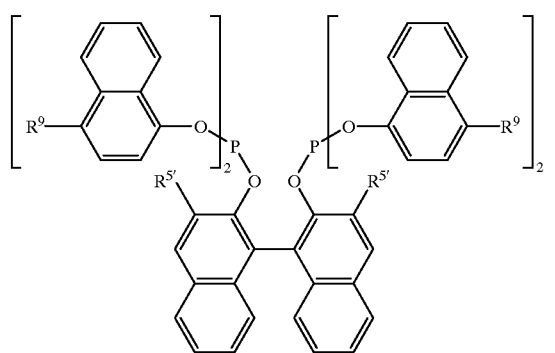

Formula VI

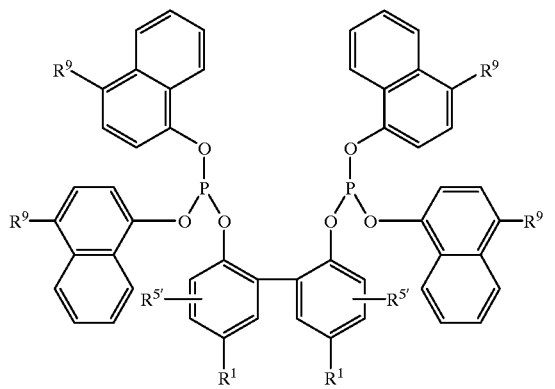

Formula VII

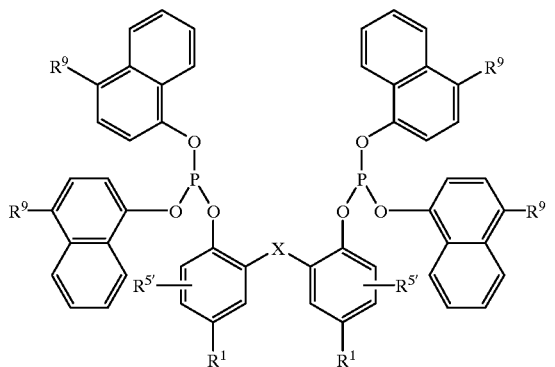

Formula VIII

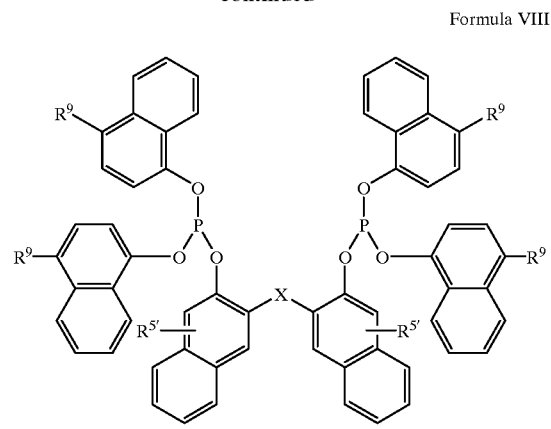

Formula IX

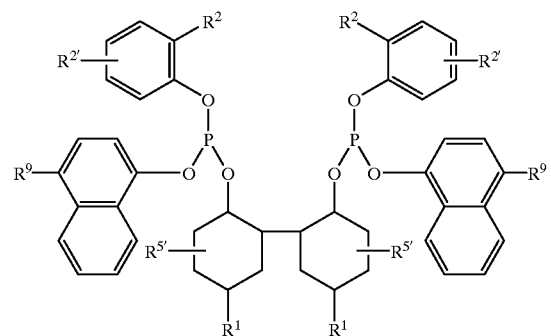

Formula X

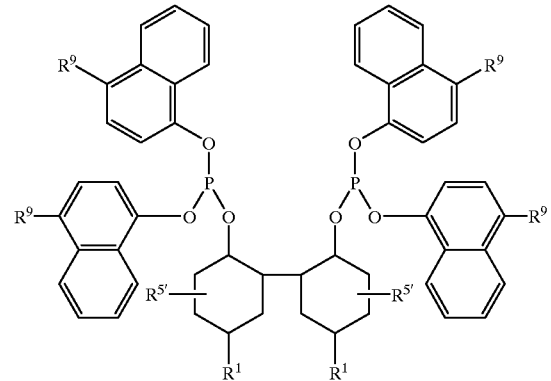

wherein
  each $R^1$ is independently a H, halogen, primary, secondary, or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
  each $R^2$ and $R^{2'}$ are independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; when $R^{2'}$ is not hydrogen, $R^{2'}$ cannot be ortho to the oxygen;
  each $R^{5'}$ is independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
  each $R^9$ is independently H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; and each X is independently O or $CH(R^{4'})$, wherein $R^{4'}$ is H, aryl, or a $C_1$ to $C_{12}$ alkyl.

The present invention provides an improved process for the liquid phase hydrocyanation of diolefinic compounds, reacting an acyclic aliphatic diolefinic compound, preferably butadiene, with a source of HCN, wherein the improvement comprises conducting the hydrocyanation in the presence of a catalyst precursor composition comprising zero-valent nickel and at least one multidentate phosphite ligand selected from the group consisting of compounds represented by Formulas I, II, III, IV, V, VI, VII, VIII, IX and X, as set forth below:

Formula I
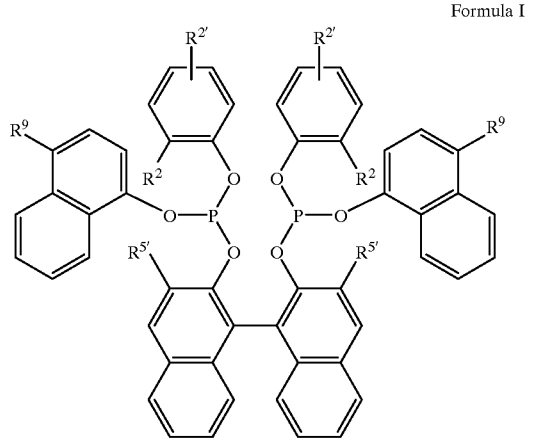

Formula II
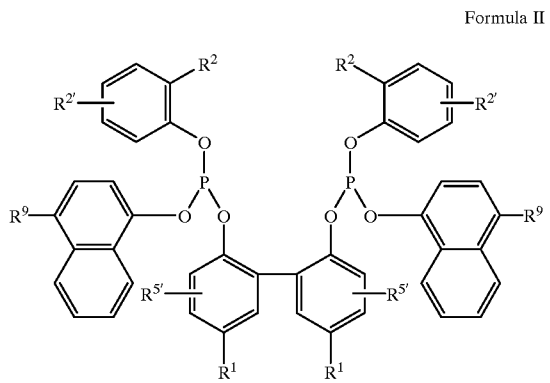

Formula III
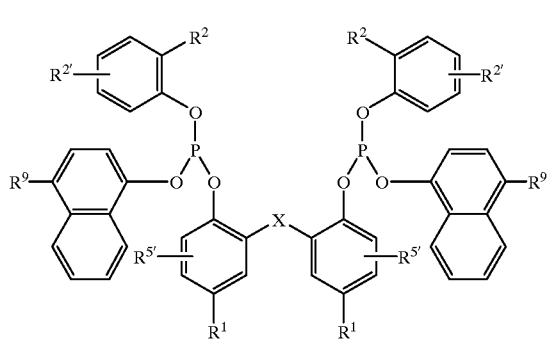

Formula IV
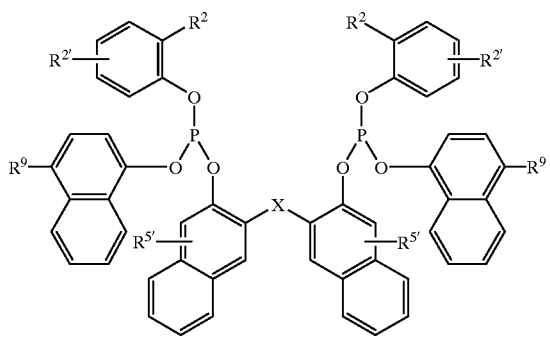

Formula V
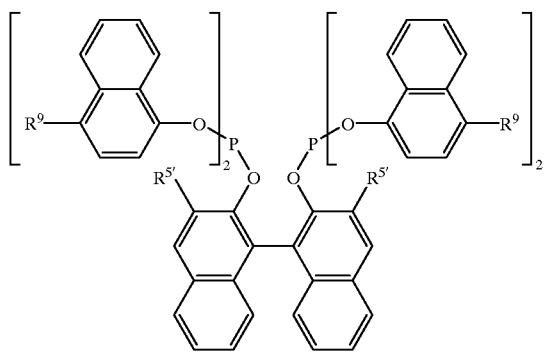

Formula VI
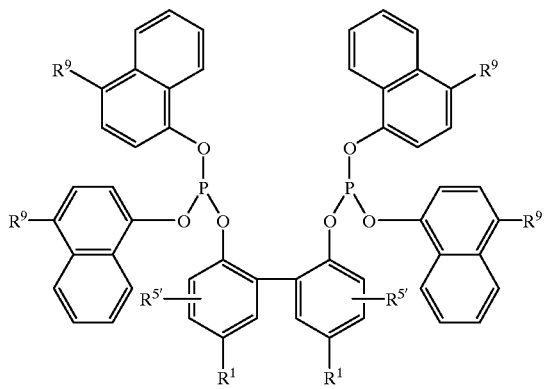

Formula VII
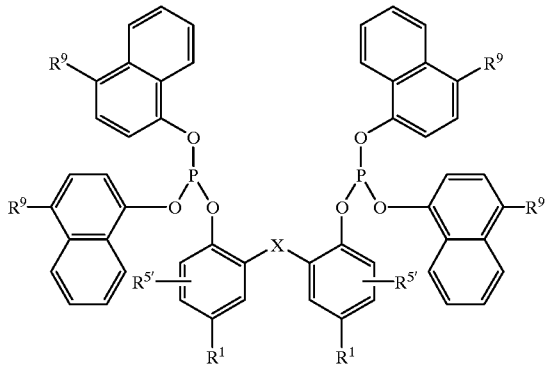

-continued

Formula VIII

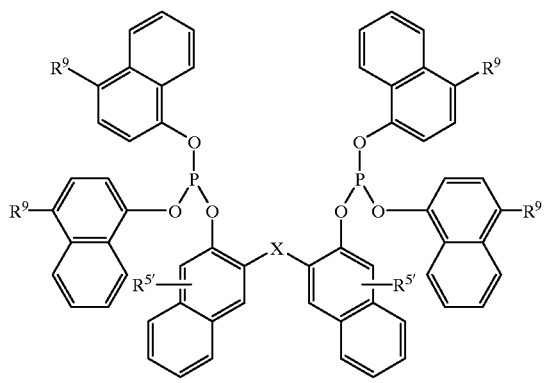

Formula IX

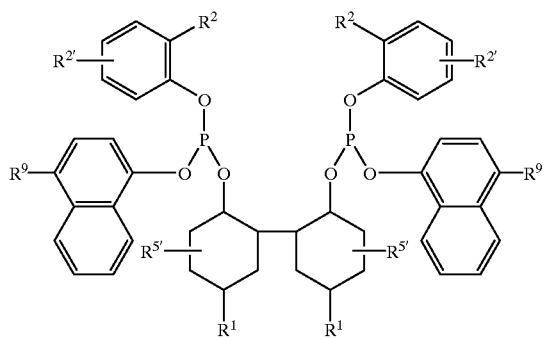

Formula X

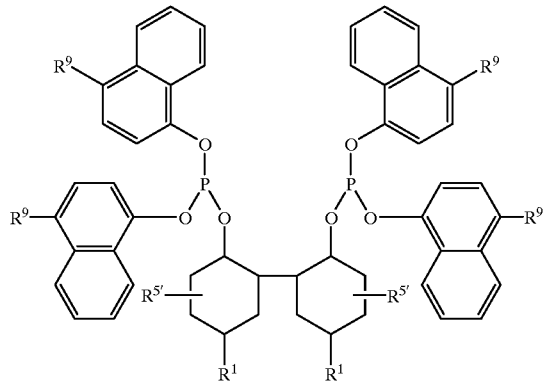

wherein
  each $R^1$ is independently a H, halogen, primary, secondary, or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
  each $R^2$ and $R^{2'}$ are independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; when $R^{2'}$ is not hydrogen, $R^{2'}$ cannot be ortho to the oxygen;
  each $R^{5'}$ is independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
  each $R^9$ is independently H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; and each X is independently O or $CH(R^{4'})$, wherein $R^{4'}$ is H, aryl, or a $C_1$ to $C_{12}$ alkyl.

As used herein, the terms "secondary" and "tertiary" refer to the carbon atom bonded to an aromatic ring.

The reactions are most conveniently performed continuously from hydrocyanation of the starting diolefin to the final 3- and/or 4-monoalkene linear nitrites. However, the processes can be conducted stepwise, i.e., the nonconjugated acyclic nitrites resulting from the hydrocyanation can be isolated per se, prior to isomerization. Furthermore, nonconjugated acyclic nitrites prepared by any method can be used as starting materials for the isomerization in accordance with this invention.

The invention also provides for certain multidentate phosphite ligands and catalyst precursor compositions made therefrom useful in these processes. In particular, these include the ligands of Formulas I–IV and VI–X.

Catalyst precursor compositions consisting of zero-valent nickel and at least one multidentate phosphite ligand according to Formula I–X are also covered.

DETAILED DESCRIPTION OF THE PREFERRED EMBODIMENTS

The catalyst precursor compositions useful in the processes of the invention are comprised of a multidentate phosphite ligand and zero-valent nickel.

The catalyst composition is referred to as a "precursor" only to indicate in all likelihood, during the hydrocyanation reaction the structure of the active catalyst composition may in fact be complexed to an olefin.

These ligands may be prepared by a variety of methods known in the art, for example, see descriptions in WO 93,03839, U.S. Pat. No. 4,769,498; U.S. Pat. No. 4,688,651, *J Amer. Chem. Soc.*, 1993, 115, 2066. The reaction of di-(1-naphthyl)-phosphorochloridite with 1,1'-binaphthol in the presence of triethylamine gives a ligand according to Formula V.

The phosphorochloridite may be prepared by a variety of methods known in the art, for example, see descriptions in *Polymer*, 1992, 33, 161; *Inorganic Syntheses*, 1966, 8, 68; U.S. Pat. No. 5,210,260; *Z. Anorg. Alig. Chem.*, 1986, 535, 221. With bulky ortho-substituted phenols (e.g., 2-t-butylphenol), phosphorochloridites can be prepared in situ from $PCl_3$ and the phenol. With less bulky groups, purification by high vacuum distillation is typically necessary. High vacuum distillation is difficult for large scale operations.

An improved process for preparing the phosphorochloridite comprises treatment of N,N-dialkyl diarylphosphoramidite derivatives with HCl. $ClP(OMe)_2$ has been prepared in this manner, see Z. *Naturforsch*, 1972, 27B, 1429; phosphorochlorides derived from substituted phenols have been prepared using this procedure as described in copending, commonly assigned, application Ser. No. 08/563,718 filed Nov. 28,1995. N,N-dialkyl diarylphos-phoramidites may be prepared by methods known in the art, for example, see descriptions in *Tetrahedron Letters*, 1993, 34, 6451 and *Aust. J Chem*, 1991, 233. It has also been found that phosphorochlorodite of 1-naphthol can be prepared in situ from $PCl_3$ and 1-napthol.

The zero-valent nickel can be prepared or generated according to techniques known in the art (U.S. Pat. No. 3,496,217; 3,631,191; 3,846,461; 3,847,959; and 3,903,120 which are incorporated herein by reference). Zero-valent nickel compounds that contain ligands which can be displaced by the organophosphorus ligand are a preferred source of zero-valent nickel. Two such preferred zero-valent nickel compounds are Ni(COD)$_2$ (COD is 1,5-cyclooctadiene) and Ni(P(O-o-C$_6$H$_4$CH$_3$)$_3$)$_2$(C$_2$H$_4$), both of which are known in the art. Alternatively, divalent nickel compounds may be combined with a reducing agent, and are then able to serve as suitable sources of zero-valent nickel in the reaction. Suitable divalent nickel compounds include compounds of the formula NiY$_2$ where Y is halide, carboxylate, or acetylacetonate. Suitable reducing agents include metal borohydrides, metal aluminum hydrides, metal alkyls, Zn, Fe, Al, Na, or H$_2$. Elemental nickel, preferably nickel powder, when combined with a halogenated catalyst, as described in U.S. Pat. No. 3,903,120, is also a suitable source of zero-valent nickel.

The actual catalyst precursor is a complex of zero-valent nickel with the multidentate phosphite ligand, which is formed when those two materials are combined. An effective catalyst typically requires at least two moles of P atoms for one gram-atom of zero-valent nickel.

The diolefinic compounds reactants used in this invention include primarily conjugated diolefins containing from 4 to 10 carbon atoms; for example, 1,3-butadiene and cis and trans-2,4-hexadienes. Butadiene is especially preferred by reason of its commercial importance in the production of adiponitrile. Other suitable diolefinic compounds include diolefinic compounds substituted with groups which do not deactivate the catalyst, for example, cis and trans-1,3-pentadienes.

The following Formulas XI and XII illustrate suitable representative starting diolefinic compounds; and Formulas XIII, XIV, and XV represent the products obtained from 1,3-butadiene and HCN.

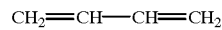

(1, 3-butadiene)

XI

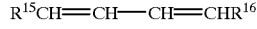

XII wherein each one of R$^{15}$ and R$^{16}$, independently, is H or a C$_1$ to C$_3$ alkyl.

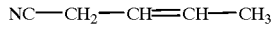

(3PN)

XIII

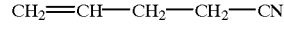

(4PN)

XIV

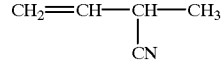

(2M3BN)

XV

It will be recognized that Compound XI is a special case of Formula XII, where each one of R$^{15}$ and R$^{16}$ is hydrogen.

In the practice of the hydrocyanation of the diolefin in accordance with the present invention, the following description applies:

The hydrocyanation reaction can be carried out with or without a solvent. The solvent should be a liquid at the reaction temperature and inert towards the unsaturated compound and the catalyst. Generally, such solvents are hydrocarbons such as benzene, xylene, or nitrites such as acetonitrile, benzonitrile, or adiponitrile.

The exact temperature used is dependent, to a certain extent, on the particular catalyst being used, the particular unsaturated compound being used and the desired rate. Generally, temperatures of from −25° C. to 200° C., can be used with from 0° C. to 150° C., being the preferred range.

The reaction may be carried out by charging a reactor with all of the reactants or preferably the reactor is charged with the catalyst or catalyst components, the unsaturated compound and whatever solvent is to be used and the hydrogen cyanide gas is swept over the surface of the reaction mixture or bubbled through said reaction mixture. If desired, when using a gaseous unsaturated organic compound, the hydrogen cyanide and the unsaturated organic compound may be fed together into the reaction medium. The molar ratio of HCN to catalyst generally is varied from about 10:1 to 100,000:1, preferably 100:1 to 5,000:1, for a batch operation. In a continuous operation, such as when using a fixed bed catalyst type of operation, a higher proportion of catalyst may be used such as 5:1 to 100,000:1, preferably 100:1 to 5,000:1, HCN to catalyst.

Preferably, the reaction mixture is agitated, such as by stirring or shaking. The cyanated product can be recovered by conventional techniques such as crystallization of the product from solution or by distillation.

One can either isolate the 2-alkyl-3-monoalkenenitriles produced by the hydrocyanation of the diolefin or proceed continuously with the isomerization under similar reaction conditions.

The 2-alkyl-3-monoalkenenitriles used as the starting materials in the isomerization of this invention can result from the hydrocyanation of diolefin described above or can come from any other available source. The olefinic double bond in the 2-alkyl-3-monoalkenenitriles used as the starting materials in the isomerization of this invention cannot be conjugated to the triple bond of the cyano group. Suitable starting 2-alkyl-3-monoalkenenitriles can also carry groups which do not attack the catalyst, for example, another cyano group. Preferably, the starting 2-alkyl-3-monoalkenenitriles contain from 5 to 8 carbon atoms, excluding any additional substitution. 2-Methyl-3-butenenitrile is especially important in the production of adiponitrile. Other representative nitrites include 2-ethyl-3-butenenitrile and 2-propyl-3-butenenitrile.

The following Formulas XVI and XVII illustrate suitable representative starting 2-alkyl-3-monoalkenenitriles. When the starting nitrile is 2-methyl-3-butenenitrile, the isomerization products are those shown in Formulas XVIII and XIX.

Formula XVI

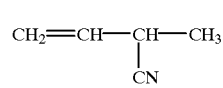

Formula XVII

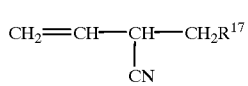

wherein $R^{17}$ is H or a $C_1$ to $C_3$ alkyl.

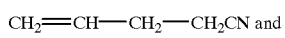 Formula XVIII

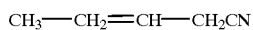 Formula XIX

It will be recognized that Formula XVI is a special case of Formula XVII, where $R^{17}$ is hydrogen.

The isomerization process of this invention can be carried out, for example, at atmospheric pressure and at any temperature in the range of 10–200° C., preferably in the range 60–150° C. The pressure is not critical, however, and can be above or below atmospheric pressure if desired. Any of the conventional batch or continuous flow procedures may be used either in the liquid phase or in the vapor phase (with respect to the relatively volatile 2-methyl-3-butenenitrile reactant and linear pentenenitrile products). The reactor may be of any mechanically and chemically resistant material, and is usually of glass or an inert metal or alloy, e.g., nickel, copper, silver, gold, platinum, stainless steel, Monel®, Hastelloy®, etc.

The process is usually carried out "neat", i.e., without an added diluent or solvent. Any solvent or diluent that is nondestructive of the catalyst can be used, however. Suitable solvents include aliphatic or aromatic hydrocarbons (hexane, cyclohexane, benzene), ethers (diethyl ether, tetrahydrofuran, dioxane, glycol dimethyl ether, anisole), esters (ethyl acetate, methyl benzoate), nitriles (acetonitrile, benzonitrile), etc.

A nonoxidizing environment is desirable in order to retard oxidative deactivation of the catalyst. Accordingly, an inert atmosphere, e.g., nitrogen, is normally and preferably used, although air may be used if desired at the expense of loss of a proportion of the catalyst through oxidation.

When the process is a typical batch operation in the liquid phase with or without a solvent, the catalytic nickel complex is soluble to some extent at temperatures within the operable range and is usually completely soluble at the most preferred operating temperature. However, the nickel complex is essentially nonvolatile, whereas the 2-methyl-3-butenenitrile reactant and the linear pentenenitrile products are relatively volatile. Accordingly, in a continuous flow procedure the catalyst may be a component of the flowing system in a completely liquid-phase operation, it may be in a mobile nonflowing liquid state in a semi-vapor phase operation, or it may be in a fixed-bed state (usually on a solid support) in a conventional flowing vapor-phase operation.

The time element in the process is not critical, and may generally be governed by practical considerations. The time required for a practical level of conversion of 2-methyl-3-butenenitrile to linear pentenenitriles is dependent upon the temperature of reaction, i.e., operation at lower temperature generally requires a longer time than operation at a higher temperature. A practical reaction time can be in the range of a few seconds to many hours, depending on the particular conditions and method of operation.

The molar ratio of 2-methyl-3-butenenitrile to catalyst is generally greater than 1:1, usually in the range from about 5:1 to 20,000:1, preferably 100:1 to 5,000:1, for a batch or continuous operation.

GENERIC EXAMPLES

The invention will now be illustrated by the following non-limiting examples of certain embodiments thereof, wherein all parts, proportions, and percentages are by weight, unless otherwise indicated.

In the following examples, stock solutions of reactants and catalyst were made in the following manner:

1,3-Butadiene Solution (BD): 25 wt % solutions of butadiene were made by vacuum transfer of a known quantity of butadiene into a three-fold amount of toluene. The resulting solutions were stored in a sealed vessel at −35° C. until their use in experiments.

HCN Solution: 25 wt % solutions of HCN were typically made by weighing 2.00 g of liquid HCN into 6.00 g of valeronitrile, in a glovebox. The resulting solutions were stored at −35° C. until their use in experiments.

Catalyst Solution: For a typical multidentate phosphite ligand, 0.84 mmol of P atoms and 0.039 g of $Ni(COD)_2$ (0.14 mmol) were mixed in either toluene or tetrahydrofuran such that the total solution weight would be 5.00 g. The resulting catalyst solutions were typically used immediately after mixing.

2-Methyl-3-butenenitrile Mixture (2M3BN): Samples of 2M3BN were obtained as mixtures of pentenenitrile isomers, which contains 81–82% 2M3BN from Fluka Chemical Corp. (Ronkonkoma, N.Y.) and distilled under nitrogen. Valeronitrile was added as internal standard at the 8 wt % level typically by mixing 0.80 g of valeronitrile and 9.20 g of the distilled 2M3BN.

In the examples as shown in Table 1, the butadiene hydrocyanation experiments were performed as follows. In the Table 1 examples, Examples 1–20 represent examples of the invention while Comparative Examples A–E represent the prior art.

To 4-mL septum-sealed screw-capped vials, 0.064 g of Ni catalyst solution (1.8 μmol Ni), 0.090 g of HCN stock solution (830 μmol HCN), and 0.200 g of BD stock solution (925 μmol BD) were added. The vials were sealed and placed in a hot-block reactor set at 80° C. Samples were removed at the appropriate time points and quenched by cooling to −35° C. The reaction mixtures were then diluted in diethylether ($Et_2O$) as a GC solvent for product analysis as measured against valeronitrile as an internal standard.

In the examples as shown in Table 2, the 2M3BN isomerization experiments were performed as follows. In the Table 2 examples, Examples 21–35 represent examples of the invention while Comparative Examples F–I represent the prior art.

To 4-mL septum-sealed screw-capped vials, 0.070 g of Ni catalyst solution (2.0 μmol Ni) and 0.100 g of the 2M3BN-containing mixture (930 μmol 2M3BN) were added. The vials were sealed and placed in a hot-block reactor set at 125° C. Samples were removed at the appropriate time points and diluted in $Et_2O$ for a GC solvent. The valeronitrile was used as an internal standard in the analysis and accounting of the 3PN and 2M3BN reaction product mixture.

TABLE 1

Butadiene Hydrocyanation

| Example | Structure | Time | % 2M3 | % 3PN | Total PN | 3 PN/2M3 |
|---|---|---|---|---|---|---|
| A | P(—O—C6H4—Me)3 | 01:30<br>03:00 | 4.1%<br>4.9% | 8.0%<br>10.0% | 12.1%<br>14.9% | 1.98<br>2.04 |
| B | P(—O—C6H4—Me)3 | 01:30<br>03:00 | 2.5%<br>3.6% | 4.5%<br>6.6% | 7.0%<br>10.2% | 1.83<br>1.86 |
| C | P(—O—C6H4—Me)3 | 01:30<br>03:00 | 2.8%<br>4.2% | 5.3%<br>7.8% | 8.1%<br>12.0% | 1.87<br>1.86 |
| D | P(—O—C6H4—Me)3 | 1:40 h<br>3:00 h | 3.0%<br>5.3% | 5.5%<br>10.2% | 8.5%<br>15.5% | 1.87<br>1.94 |
| E | P(—O—C6H4—Me)3 | 1:30 hr<br>3:15 hr | 3.6%<br>5.4% | 7.1%<br>11.0% | 10.7%<br>16.4% | 1.95<br>2.05 |
| 1 | [biphenyl bis-phosphite with naphthyl groups] | 01:30<br>03:00 | 37.0%<br>29.3% | 20.6%<br>16.9% | 57.6%<br>46.2% | 0.56<br>0.58 |
| 2 | [binaphthyl bis-phosphite with isopropyl ester and naphthyl groups] | 01:50<br>03:00 | 17.7%<br>26.0% | 34.8%<br>39.1% | 52.5%<br>65.0% | 1.96<br>1.50 |

TABLE 1-continued

Butadiene Hydrocyanation

| Example | Structure | Time | % 2M3 | % 3PN | Total PN | 3 PN/2M3 |
|---|---|---|---|---|---|---|
| 3 | 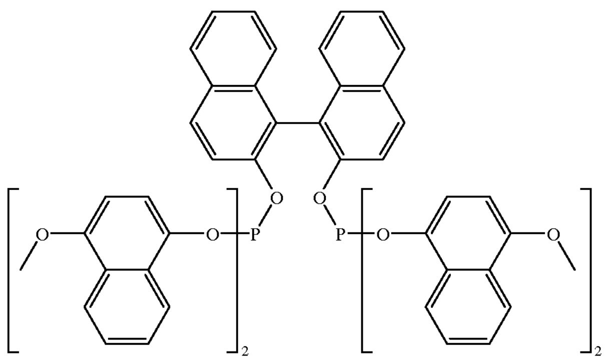 | 01:30 | 38.7% | 23.7% | 62.3% | 0.61 |
| | | 03:00 | 40.9% | 24.9% | 65.7% | 0.61 |
| 4 | 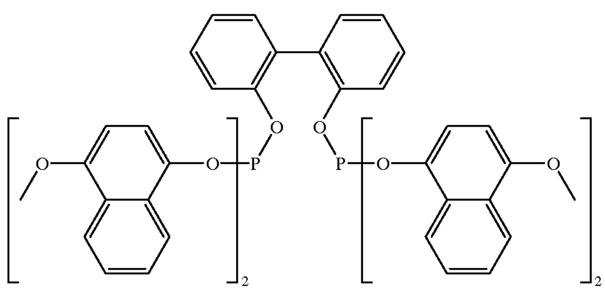 | 01:30 | 30.2% | 17.1% | 47.3% | 0.57 |
| | | 03:00 | 35.7% | 20.2% | 56.0% | 0.57 |
| 5 | 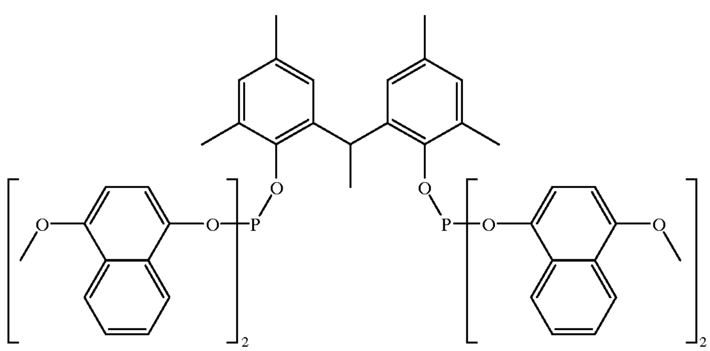 | 01:30 | 31.9% | 25.2% | 57.1% | 0.79 |
| | | 03:00 | 30.5% | 24.0% | 54.5% | 0.79 |
| 6 | 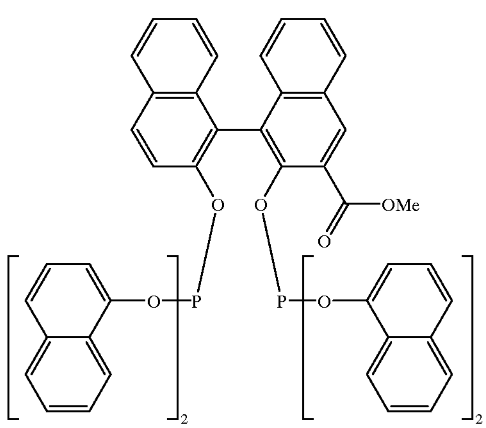 | 1:30 h | 21.9% | 30.0% | 51.9% | 1.37 |
| | | 3:00 h | 20.8% | 28.9% | 49.7% | 1.39 |

TABLE 1-continued

Butadiene Hydrocyanation

| Example | Structure | Time | % 2M3 | % 3PN | Total PN | 3 PN/ 2M3 |
|---|---|---|---|---|---|---|
| 7 | 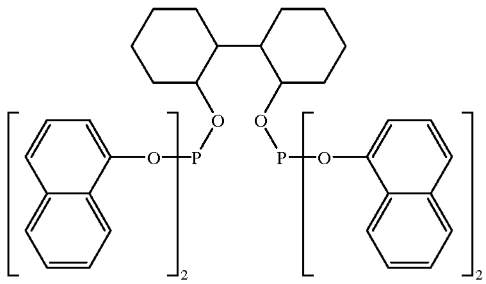 | 1:30 h<br>3:00 h | 24.7%<br>20.8% | 35.1%<br>29.7% | 59.8%<br>50.5% | 1.42<br>1.43 |
| 8 | 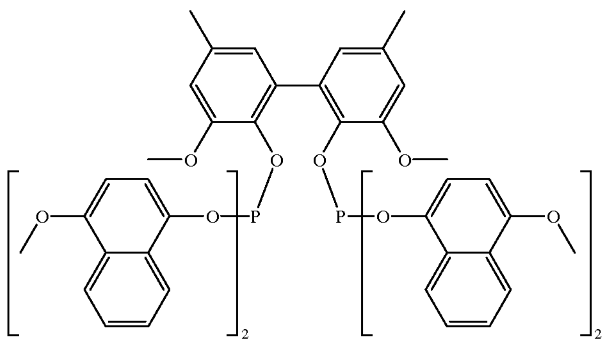 | 1:30 hr<br>3:00 hr | 22.8%<br>15.0% | 47.4%<br>50.2% | 70.2%<br>65.2% | 2.08<br>3.35 |
| 9 | 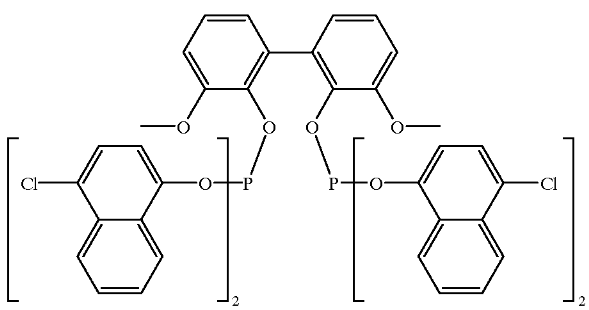 | 1:30 hr<br>3:00 hr | 29.2%<br>37.5% | 16.7%<br>21.1% | 45.9%<br>58.6% | 0.57<br>0.56 |
| 10 | 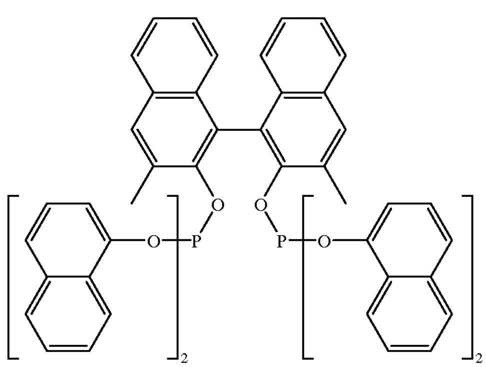 | 1:30 hr<br>3:00 hr | 19.3%<br>21.0% | 45.6%<br>48.4% | 64.8%<br>69.4% | 2.36<br>2.30 |

TABLE 1-continued

Butadiene Hydrocyanation

| Example | Structure | Time | % 2M3 | % 3PN | Total PN | 3 PN/2M3 |
|---|---|---|---|---|---|---|
| 11 | 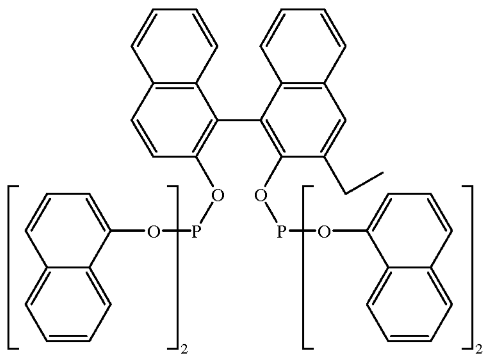 | 1:30 hr<br>3:00 hr | 32.6%<br>38.9% | 34.5%<br>40.0% | 67.1%<br>78.9% | 1.06<br>1.03 |
| 12 | 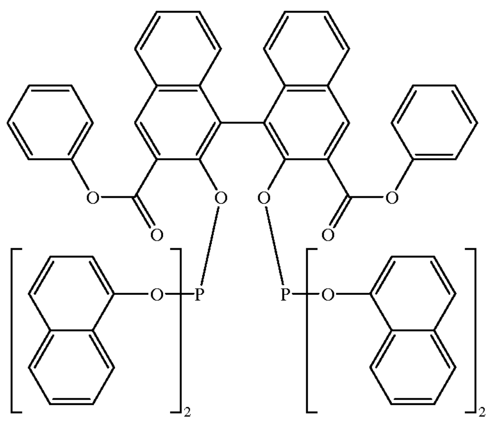 | 1:30 hr<br>3:00 hr | 22.0%<br>14.6% | 46.1%<br>49.9% | 68.1%<br>64.5% | 2.10<br>3.42 |
| 13 | 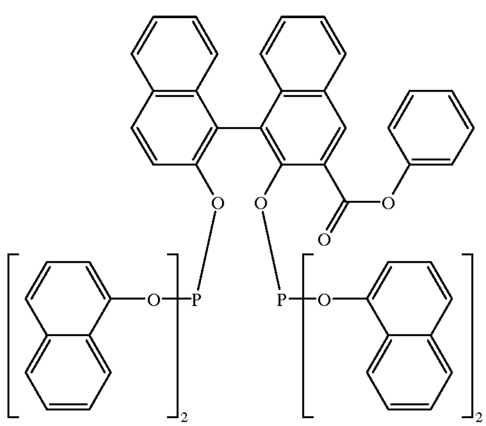 | 1:30 hr<br>3:00 hr | 29.0%<br>29.3% | 38.2%<br>44.7% | 67.2%<br>74.0% | 1.31<br>1.53 |

TABLE 1-continued

Butadiene Hydrocyanation

| Example | Structure | Time | % 2M3 | % 3PN | Total PN | 3 PN/ 2M3 |
|---|---|---|---|---|---|---|
| 14 | 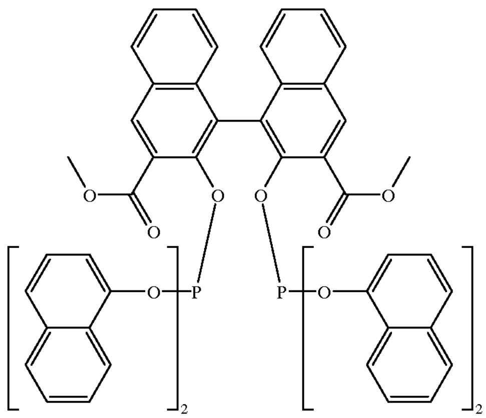 | 1:30 hr | 27.2% | 48.1% | 75.3% | 1.77 |
| | | 3:00 hr | 26.1% | 52.0% | 78.1% | 1.99 |
| 15 | 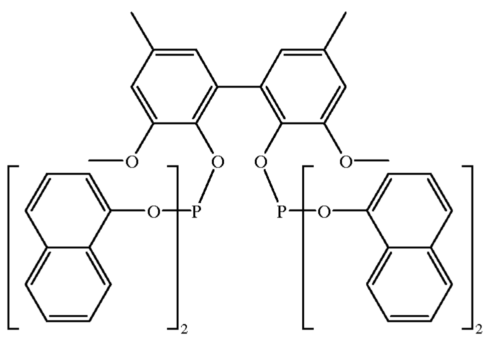 | 1:30 hr | 30.4% | 47.9% | 78.4% | 1.57 |
| | | 3:00 hr | 15.5% | 66.1% | 81.6% | 4.26 |
| 16 | 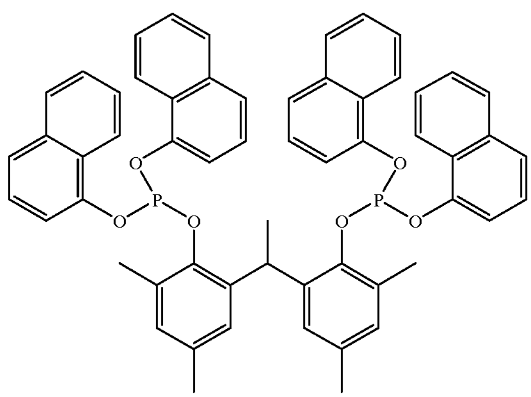 | 1:30 hr | 45.4% | 34.2% | 79.6% | 0.75 |
| | | 3:00 hr | 39.3% | 32.0% | 71.3% | 0.81 |

TABLE 1-continued

Butadiene Hydrocyanation

| Example | Structure | Time | % 2M3 | % 3PN | Total PN | 3 PN/ 2M3 |
|---|---|---|---|---|---|---|
| 17 | 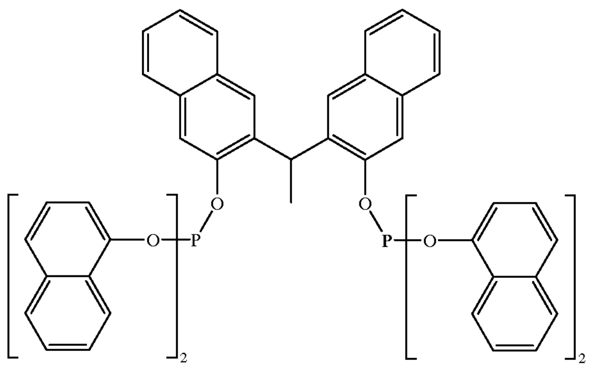 | 1:30 hr<br>3:00 hr | 25.6%<br>24.3% | 13.8%<br>13.2% | 39.4%<br>37.5% | 0.54<br>0.54 |
| 18 | 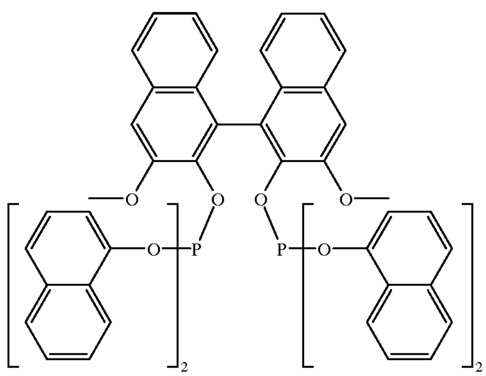 | 01:30<br>03:00 | 26.2%<br>27.0% | 43.6%<br>48.2% | 68.8%<br>75.2% | 1.62<br>1.79 |
| 19 | 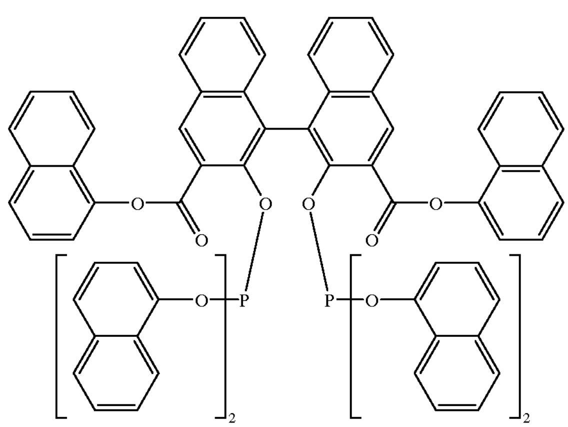 | 1.5 hr<br>3.0 hr | 19.6%<br>14.3% | 45.4%<br>50.1% | 65.0%<br>64.4% | 2.32<br>3.52 |

TABLE 1-continued
Butadiene Hydrocyanation
| Example | Structure | Time | % 2M3 | % 3PN | Total PN | 3 PN/2M3 |
|---|---|---|---|---|---|---|
| 20 | 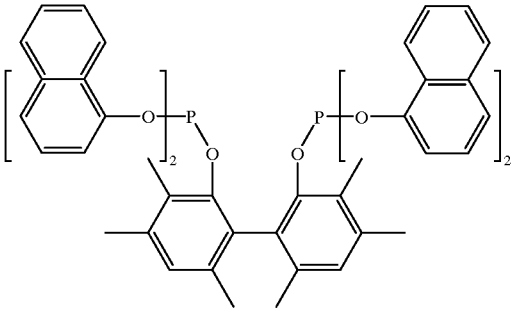 | 1.5 hr<br>3.0 hr | 12.3%<br>22.8% | 39.4%<br>57.4% | 51.7%<br>80.2% | 3.19<br>2.51 |
TABLE 2
Isomerization of 2-Methyl-3-Butenenitrile
| Example | Structure | Time | % 2M3 | % 3PN | 3PN/2M3 |
|---|---|---|---|---|---|
| F | 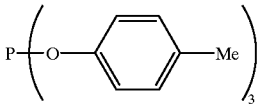 | 01:30<br>03:00 | 81.1%<br>52.3% | 20.9%<br>42.8% | 0.26<br>0.82 |
| G | 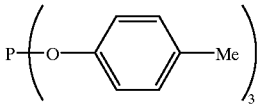 | 01:30<br>03:00 | 89.6%<br>72.3% | 10.8%<br>24.7% | 0.12<br>0.34 |
| H | 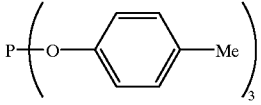 | 01:30<br>03:00 | 78.9%<br>83.9% | 11.9%<br>11.8% | 0.15<br>0.14 |
| I | 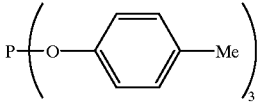 | 1:30<br>3.15 | 90.9%<br>83.7% | 8.3%<br>12.6% | 0.09<br>0.15 |
| 21 | 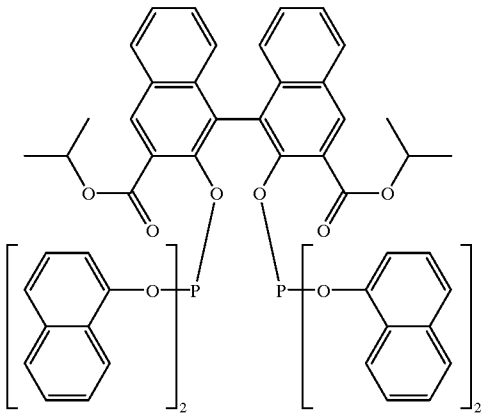 | 01:50<br>03:00 | 8.2%<br>9.1% | 93.3%<br>92.5% | 11.39<br>10.14 |

TABLE 2-continued

Isomerization of 2-Methyl-3-Butenenitrile

| Example | Structure | Time | % 2M3 | % 3PN | 3PN/2M3 |
|---|---|---|---|---|---|
| 22 | 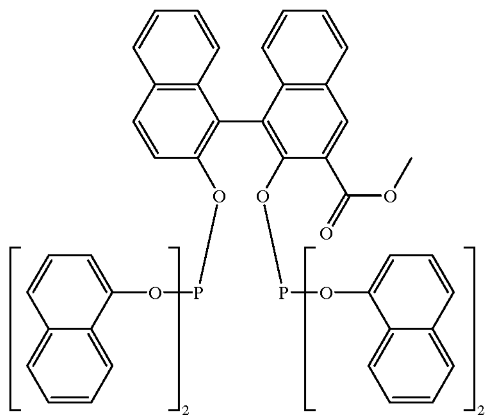 | 1:30 h<br>3:00 h | 18.7%<br>8.0% | 82.5%<br>93.1% | 4.40<br>11.67 |
| 23 | 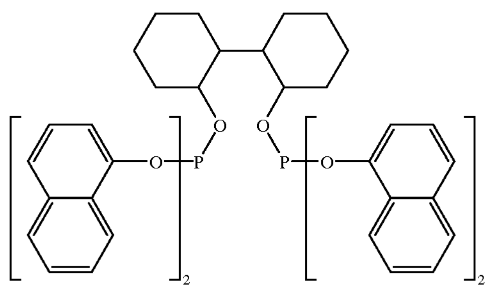 | 1:30 h<br>3:00 h | 19.5%<br>11.9% | 78.0%<br>86.8% | 4.01<br>7.28 |
| 24 | 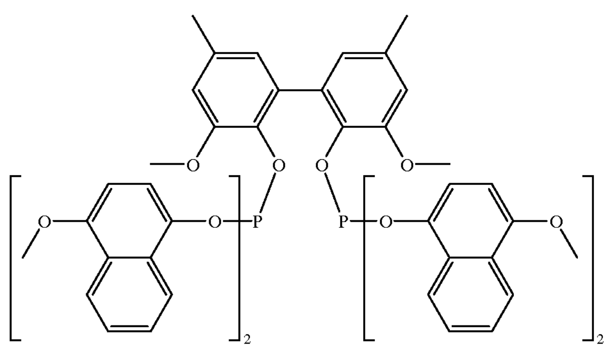 | 1.30 hr<br>3:00 hr | 5.8%<br>5.8% | 95.1%<br>94.9% | 16.29<br>16.34 |
| 25 | 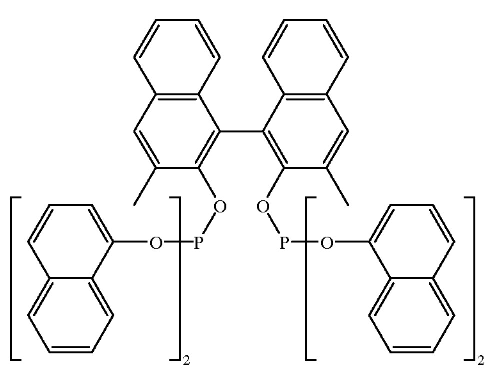 | 1:30 hr<br>3:00 hr | 7.7%<br>6.2% | 93.7%<br>94.9% | 12.11<br>15.28 |

TABLE 2-continued

Isomerization of 2-Methyl-3-Butenenitrile

| Example | Structure | Time | % 2M3 | % 3PN | 3PN/2M3 |
|---|---|---|---|---|---|
| 26 | 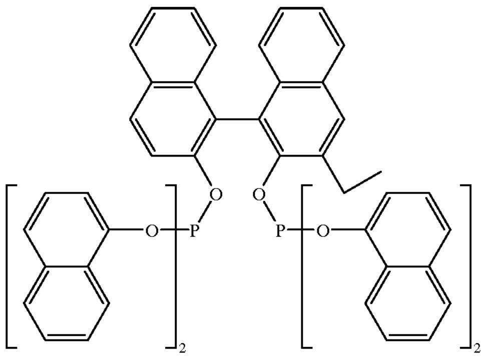 | 1:30 hr<br>3:00 hr | 43.9%<br>33.1% | 56.2%<br>66.7% | 1.28<br>2.02 |
| 27 | 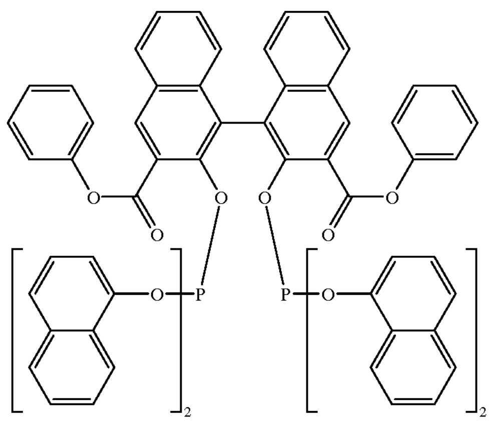 | 1:30 hr<br>3:00 hr | 42.4%<br>42.0% | 58.7%<br>58.9% | 1.38<br>1.40 |
| 28 | 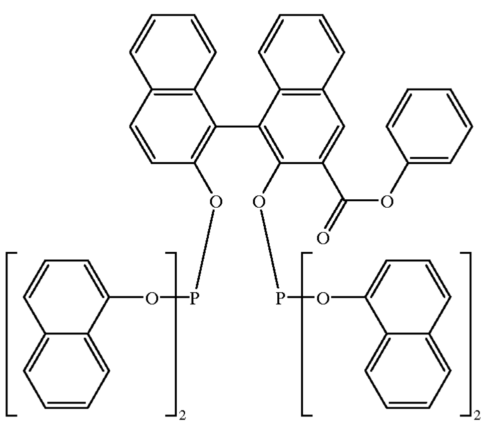 | 1:30 hr<br>3:00 hr | 15.9%<br>17.3% | 85.4%<br>83.6% | 5.37<br>4.84 |

TABLE 2-continued

Isomerization of 2-Methyl-3-Butenenitrile

| Example | Structure | Time | % 2M3 | % 3PN | 3PN/2M3 |
|---------|-----------|------|-------|-------|---------|
| 29 | 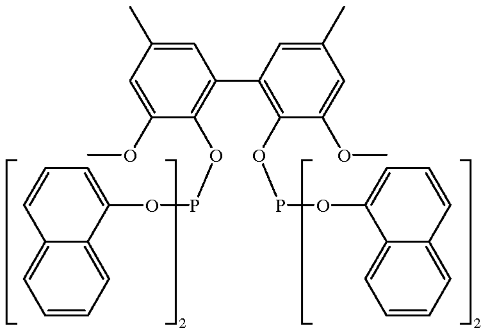 | 1:30 hr | 5.6% | 92.9% | 16.56 |
|    | | 3:00 hr | 5.5% | 93.0% | 16.88 |
| 30 | 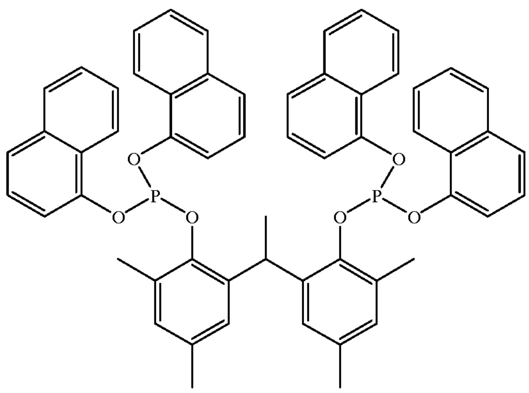 | 1:30 hr | 23.0% | 76.3% | 3.31 |
|    | | 3:00 hr | 7.2% | 92.3% | 12.89 |
| 31 | 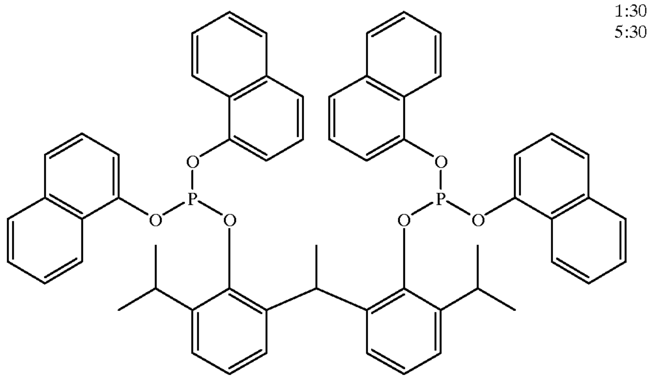 | 1:30 hr | 49.5% | 50.4% | 1.02 |
|    | | 5:30 hr | 13.8% | 84.7% | 6.14 |
| 32 | 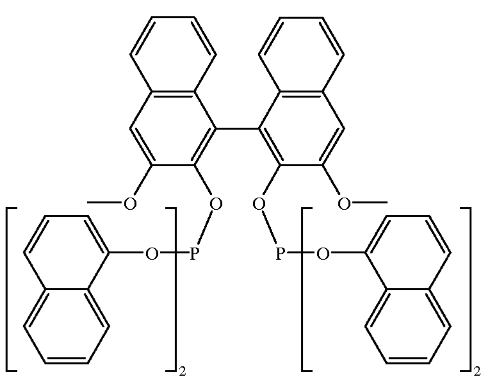 | 01:30 | 5.9% | 94.3% | 15.86 |
|    | | 03:00 | 5.9% | 93.7% | 15.98 |

TABLE 2-continued

Isomerization of 2-Methyl-3-Butenenitrile

| Example | Structure | Time | % 2M3 | % 3PN | 3PN/2M3 |
|---|---|---|---|---|---|
| 33 | | 1.5 hr | 5.5% | 88.6% | 16.04 |
|    | | 3.0 hr | 5.6% | 90.5% | 16.25 |
| 34 | 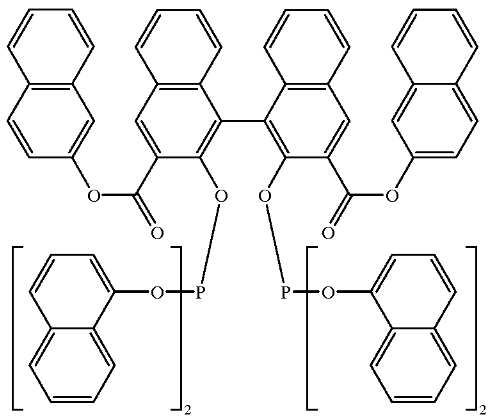 | 1.5 hr | 41.7% | 54.4% | 1.30 |
|    | | 3.0 hr | 39.4% | 57.4% | 1.46 |
| 33 | | 1.5 hr | 6.4% | 92.9% | 14.58 |
|    | | 3.0 hr | 6.1% | 92.9% | 15.35 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. An improved process for the liquid phase hydrocyanation of diolefinic compounds and subsequent isomerization of the resulting nonconjugated 2-alkyl-3-monoalkenenitriles comprising reacting an acyclic aliphatic diolefinic compound with a source of HCN; the improvement comprising conducting the hydrocyanation and subsequent isomerization in the presence of a catalyst precursor composition comprising zero-valent nickel and at least one multidentate phosphite ligand selected from the group consisting of compounds represented by Formulas I, II, III, IV, V, VI, VII, VIII, IX and X, as set forth below:

Formula I
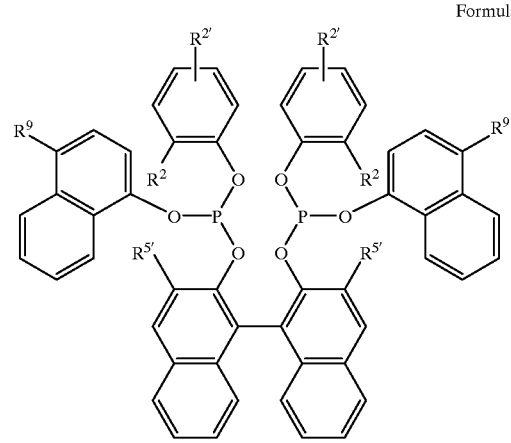
Formula V
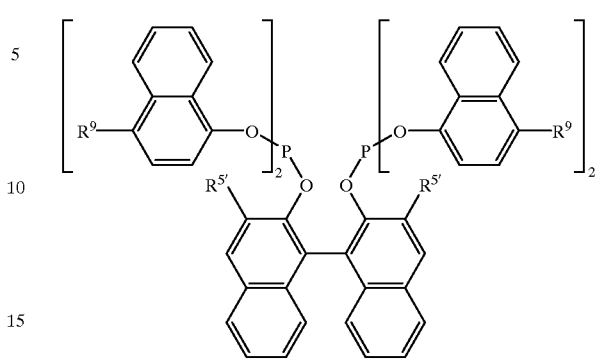
Formula II
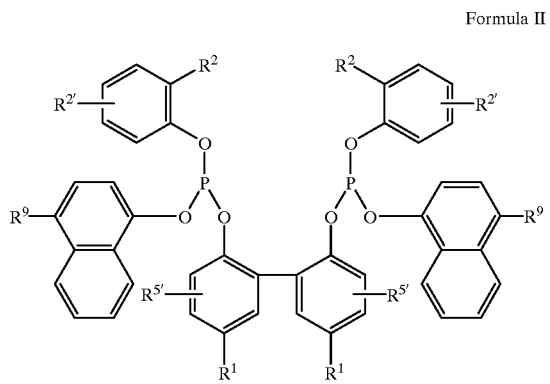
Formula VI
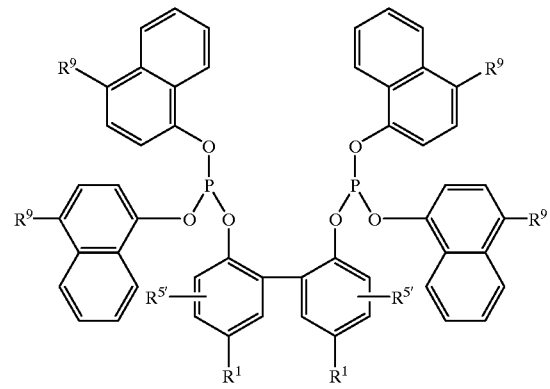
Formula III
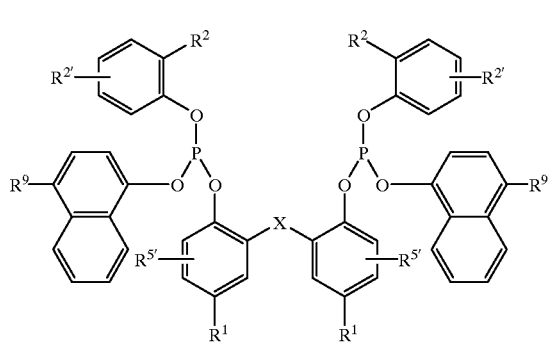
Formula VII
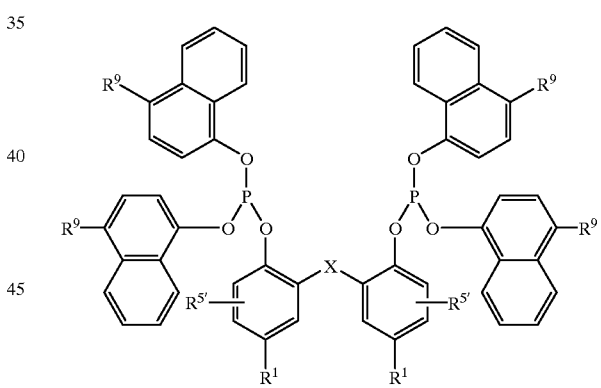
Formula IV
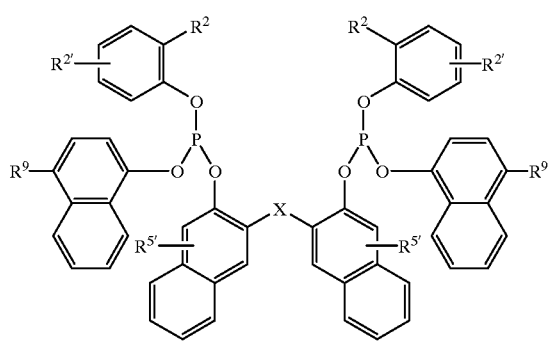
Formula VIII
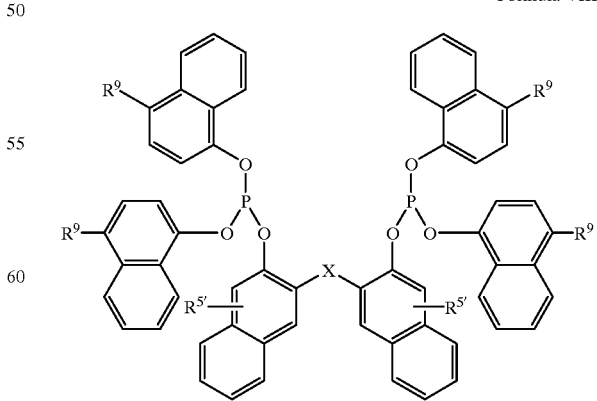

-continued

Formula IX

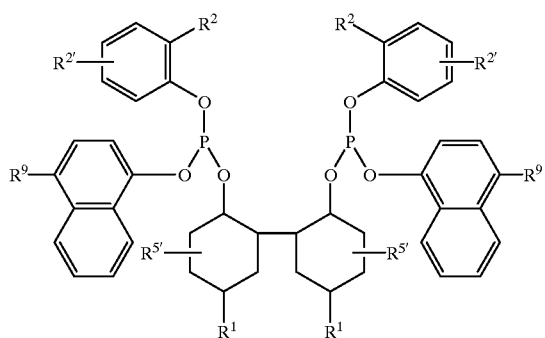

Formula X

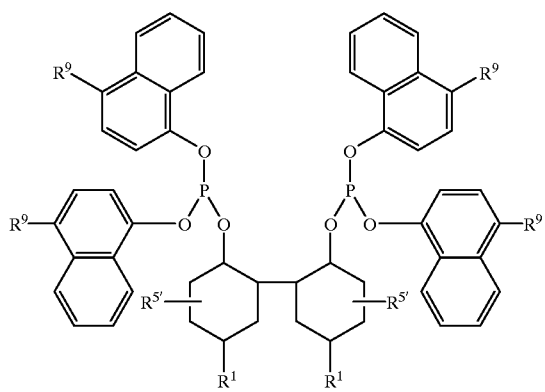

wherein
- each $R^1$ is independently a H, halogen, primary, secondary, or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
- each $R^2$ and $R^{2'}$ are independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; when $R^{2'}$ is not hydrogen, $R^{2'}$ cannot be ortho to the oxygen;
- each $R^{5'}$ is independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;
- each $R^9$ is independently H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; and
- each X is independently O or $CH(R^{4'})$, wherein $R^{4'}$ is H, aryl, or a $C_1$ to $C_{12}$ alkyl.

2. The improved process of claim 1 wherein the diolefinic compound is butadiene.

3. The improved process of claim 1 wherein either hydrocyanation or isomerization is performed as a batch operation or both hydrocyanation and isomerization are performed as a batch operation.

4. The improved process of claim 1 wherein either hydrocyanation or isomerization is performed continously or both hydrocyanation and isomerization are performed continuously.

5. The improved process of claim 1 wherein the diolefin compound comprises conjugated diolefins containing from 4 to 10 carbon atoms.

6. The improved process of claim 5 wherein the diolefin compound is selected from the group consisting of 1,3-butadiene, cis-2,4-hexadiene, trans-2,4-hexadiene, cis-1,3-pentadiene and trans-1,3-pentadiene.

7. The improved process of claim 1 wherein hydrocyanation is carried 5 out at a temperature of from about 0° C. to 150° C.

8. The improved process of claim 3 wherein during hydrocyanation the molar ratio of HCN to catalyst precursor compound is between about 100:1 to 5,000:1.

9. The improved process of claim 4 wherein during hydrocyanation the molar ratio of HCN to catalyst precursor compound is between about 100:1 to 5,000:1.

10. An improved process for the liquid phase hydrocyanation of acyclic aliphatic diolefinic compounds comprising reacting an acyclic aliphatic diolefinic compound with a source of HCN; the improvement comprising conducting the hydrocyanation reaction in the presence of a catalyst precursor composition comprising a zero-valent nickel and at least one multidentate phosphite ligand selected from the group consisting of compounds represented by Formulas I, II, III, IV, V, VI, VIII, IX and X, as set forth below:

Formula I

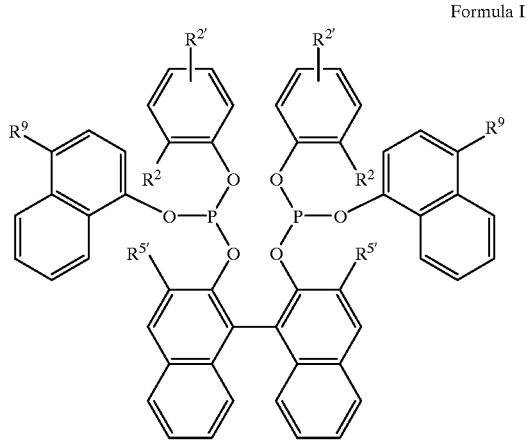

Formula II

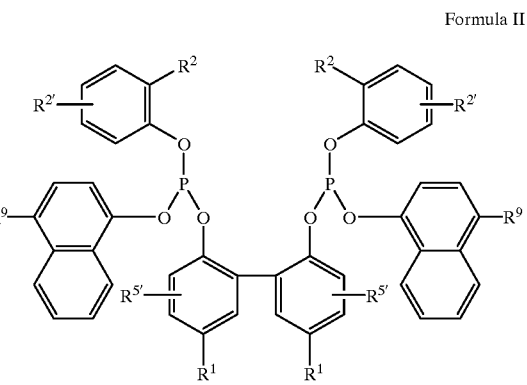

Formula III
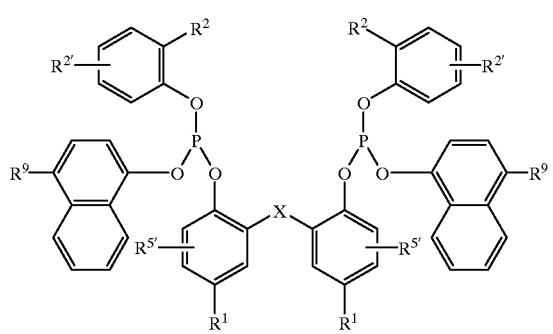
Formula IV
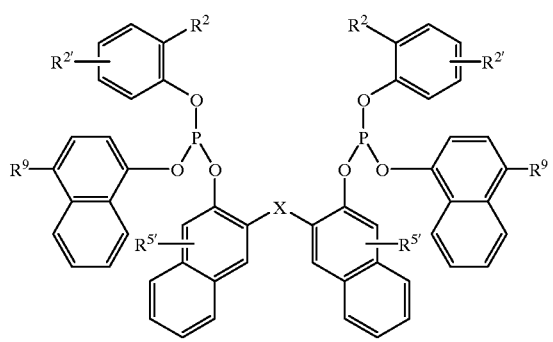
Formula V
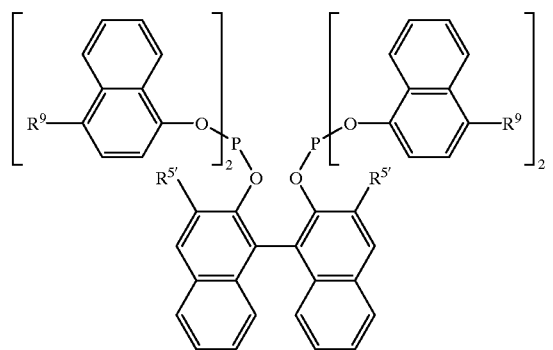
Formula VI
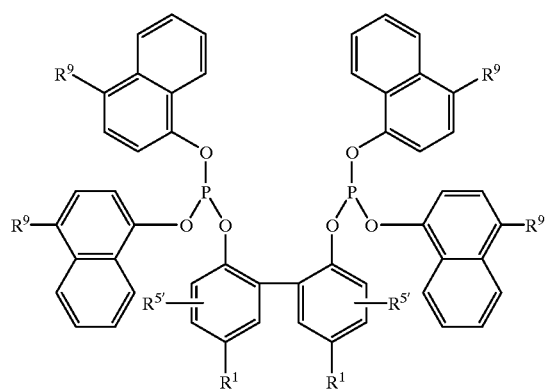
Formula VII
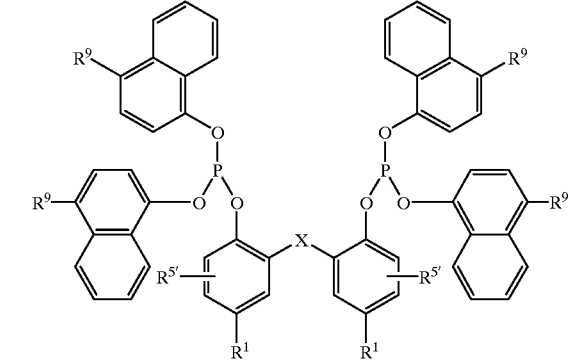
Formula VIII
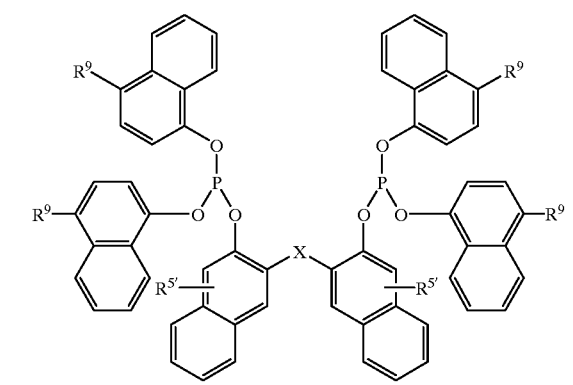
Formula IX
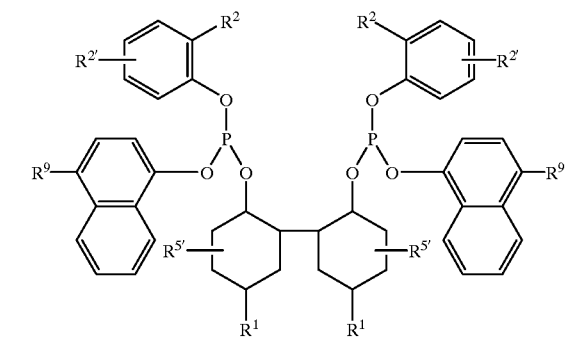
Formula X
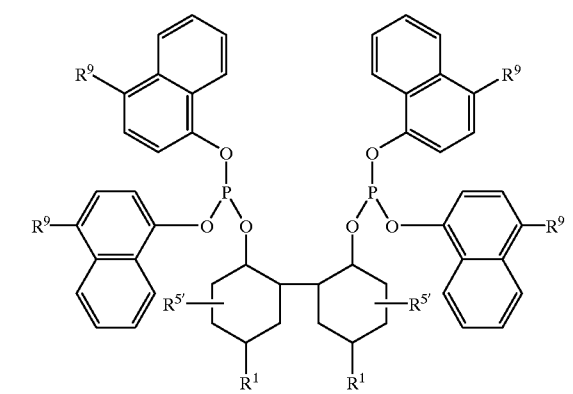

wherein

- each $R^1$ is independently a H, halogen, primary, secondary, or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;

- each $R^2$ and $R^{2'}$ are independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; when $R^{2'}$ is not hydrogen, $R^{2'}$ cannot be ortho to the oxygen;

- each $R^{5'}$ is independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;

- each $R^9$ is independently H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; and

- each X is independently O or $CH(R4')$, wherein $R^{4'}$ is H, aryl, or a $C_1$ to $C_{12}$ alkyl.

11. The improved process of claim 10 wherein the diolefinic compound is butadiene.

12. The improved process of claim 10 wherein hydrocyanation is performed as a batch operation.

13. The improved process of claim 10 wherein hydrocyanation is performed continuously.

14. The improved process of claim 10 wherein the diolefinic compound comprises conjugated diolefins containing from 4 to 10 carbon atoms.

15. The improved process of claim 14 wherein the diolefinic compound is selected from the group consisting of 1,3-butadiene, cis-2,4-hexadiene, trans-2,4-hexadiene, cis-1,3-pentadiene and trans-1,3-pentadiene.

16. The improved process of claim 10 wherein hydrocyanation is carried out at a temperature of from about 0° C. to about 150° C.

17. The improved process of claim 12 wherein the molar ratio of HCN to catalyst precursor compound is between about 100:1 to 5,000:1.

18. The improved process of claim 13 wherein the molar ratio of HCN to catalyst precursor compound is between about 100:1 to 5,000:1.

19. An improved process for the isomerization of a nonconjugated 2-alkyl-3-monoalkenenitrile, the improvement comprising carrying out the isomerization in the presence of a catalyst precursor composition comprising a zero-valent nickel and at least one multidentate phosphite ligand selected from the group consisting of compounds represented by Formulas I, II, III, IV, V, VI, VII, VIII, IX and X, as set forth below:

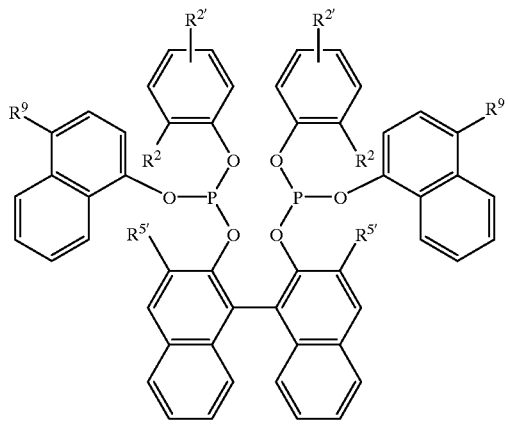

Formula I

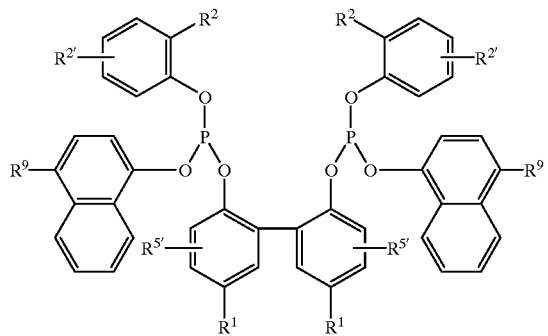

Formula II

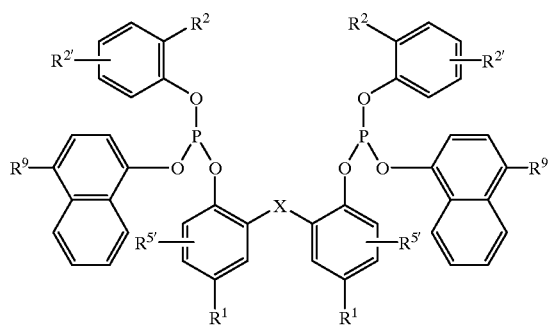

Formula III

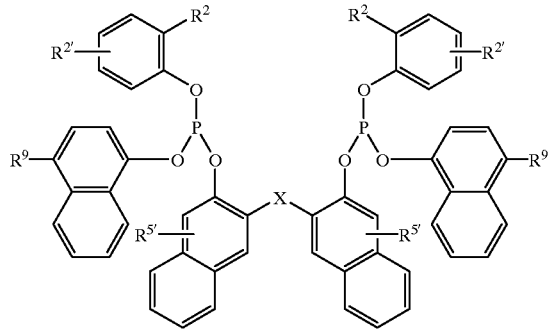

Formula IV

Formula V

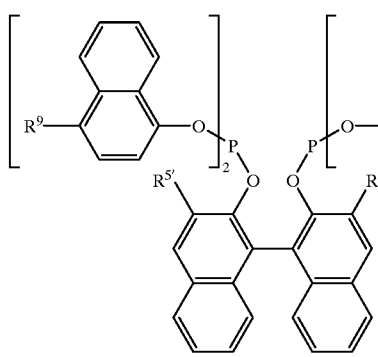

Formula VI

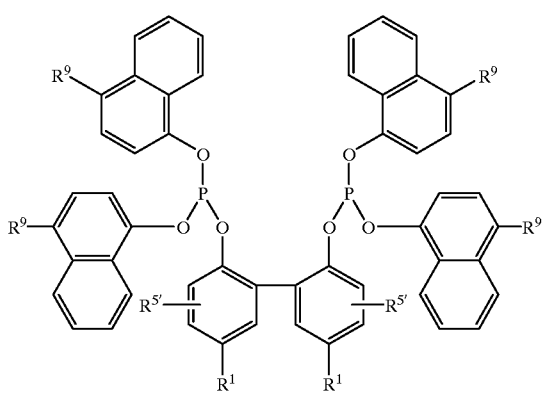

Formula VII

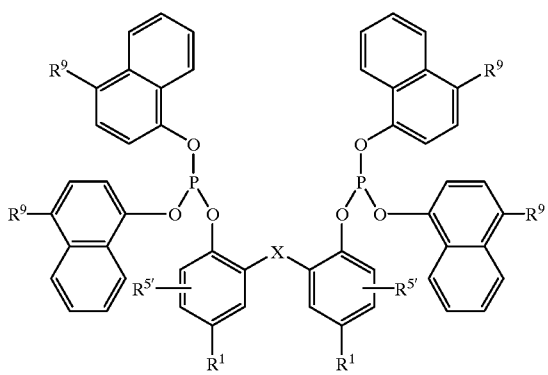

Formula VIII

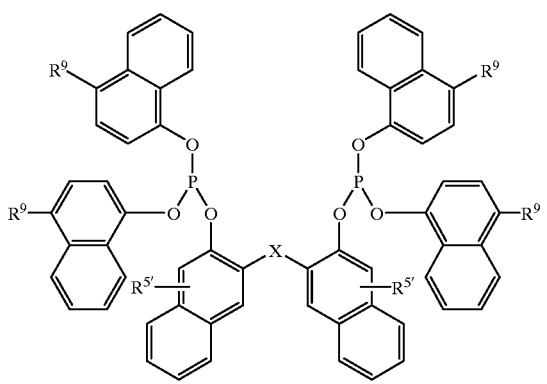

Formula IX

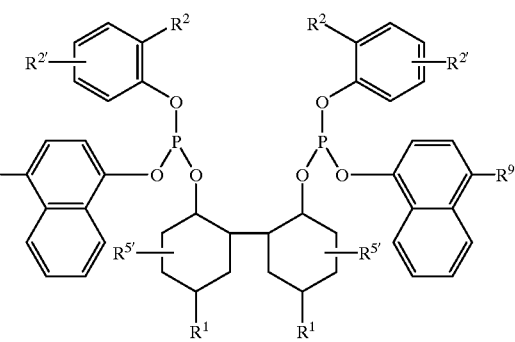

Formula X wherein each $R^1$ is independently a H, halogen, primary, secondary, or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;

each $R^2$ and $R^{2'}$ are independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; when $R^{2'}$ is not hydrogen, $R^{2'}$ cannot be ortho to the oxygen;

each $R^{5'}$ is independently a H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl;

each $R^9$ is independently H, halogen, primary, secondary or tertiary hydrocarbyl of 1 to 12 carbon atoms, $OR^3$ wherein $R^3$ is a $C_1$ to $C_{12}$ alkyl, or $CO_2R^{3'}$ wherein $R^{3'}$ is a $C_1$ to $C_{12}$ alkyl, or aryl; and each X is independently O or CH(R4'), wherein $R^{4'}$ is H, aryl, or a $C_1$ to $C_{12}$ alkyl.

20. The improved process of claim 19 wherein the non-conjugated 2-alkyl-3-monoalkenenitrile is 2-methyl-3-butenenitrile.

21. The improved process of claim 19 wherein isomerization is performed as a batch operation.

22. The improved process of claim 19 wherein isomerization is performed continuously.

23. The improved process of claim 19 wherein the nonconjugated 2-alkyl-3-monoalkenenitrile is selected from the group consisting of 2-ethyl-3-butenenitrile and 2-propyl-3-butenenitrile.

24. The improved process of claim 19 wherein isomerization is carried out at a temperature of from about 60° C. to about 150° C.

25. The improved process of claim 21 wherein the molar ratio of nonconjugated 2-alkyl-3-monoalkenenitrile to catalyst precursor compound is between about 100:1 to 5,000:1.

26. The improved process of claim 22 wherein the molar ratio of nonconjugated 2-alkyl-3-monoalkenenitrile to catalyst precursor compound is between about 100:1 to 5,000:1.

* * * * *